US 9,694,359 B2

(12) United States Patent
Losada et al.

(10) Patent No.: US 9,694,359 B2
(45) Date of Patent: Jul. 4, 2017

(54) MECHANICAL SEPARATOR FOR A BIOLOGICAL FLUID

(71) Applicant: Becton, Dickinson and Company, Franklin Lakes, NJ (US)

(72) Inventors: Robert J. Losada, Astoria, NY (US); Arun U. Nair, Whippany, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 68 days.

(21) Appl. No.: 14/629,643

(22) Filed: Feb. 24, 2015

(65) Prior Publication Data

US 2016/0136640 A1 May 19, 2016

Related U.S. Application Data

(60) Provisional application No. 62/079,216, filed on Nov. 13, 2014.

(51) Int. Cl.
*B01L 3/00* (2006.01)
*G01N 33/49* (2006.01)

(52) U.S. Cl.
CPC ........ *B01L 3/50215* (2013.01); *G01N 33/491* (2013.01); *B01L 2300/06* (2013.01); *B01L 2300/0832* (2013.01); *B01L 2400/0644* (2013.01)

(58) Field of Classification Search
CPC ......... B01L 3/50215; B01L 2300/0832; B01L 2300/06; B01L 2400/0644; G01N 33/491
See application file for complete search history.

(56) References Cited

U.S. PATENT DOCUMENTS

| 2,577,780 A | 12/1951 | Lockhart |
| 2,693,049 A | 11/1954 | Atton |
| 2,910,798 A | 11/1959 | Bias |
| 3,300,051 A | 1/1967 | Mitchell |
| 3,326,215 A | 6/1967 | Sarnoff et al. |
| 3,508,653 A | 4/1970 | Coleman |
| 3,543,338 A | 12/1970 | Cooper |

(Continued)

FOREIGN PATENT DOCUMENTS

| AT | 414209 B | 10/2006 |
| DE | 2749130 A1 | 5/1979 |

(Continued)

*Primary Examiner* — Jill Warden
*Assistant Examiner* — Julie Tavares
(74) *Attorney, Agent, or Firm* — The Webb Law Firm

(57) ABSTRACT

A separation assembly for separation of a fluid into first and second parts is disclosed. A container has a first end, a second end, and a sidewall extending therebetween defining an interior, the container defining a longitudinal axis between the first end and the second end. A separator body is disposed within the interior having a through-hole defined therethrough. The separator body includes a first part, and a second part interfaced with the first part, wherein the separator body is transitionable from a first position wherein the through-hole is provided in fluid-receiving alignment with the first end of the container, to a second position wherein the through-hole is provided substantially perpendicular to the longitudinal axis of the container. In the first position, a through-axis of the through-hole of the separator body is in a plane that is not parallel with a plane containing the longitudinal axis of the container.

27 Claims, 7 Drawing Sheets

(56) References Cited

U.S. PATENT DOCUMENTS

| | | |
|---|---|---|
| 3,647,070 A | 3/1972 | Adler |
| 3,654,925 A | 4/1972 | Holderith |
| 3,661,265 A | 5/1972 | Greenspan |
| 3,741,400 A | 6/1973 | Dick |
| 3,747,257 A | 7/1973 | Olsen |
| 3,771,965 A | 11/1973 | Grams |
| 3,773,450 A | 11/1973 | Svanfos |
| 3,779,383 A | 12/1973 | Ayres |
| 3,780,935 A | 12/1973 | Lukacs et al. |
| 3,786,985 A | 1/1974 | Blaivas |
| 3,800,947 A | 4/1974 | Smith |
| 3,809,733 A | 5/1974 | Sandiford et al. |
| 3,814,248 A | 6/1974 | Lawhead |
| 3,814,258 A | 6/1974 | Ayres |
| 3,832,110 A | 8/1974 | Hehl |
| 3,849,072 A | 11/1974 | Ayres |
| 3,850,174 A | 11/1974 | Ayres |
| 3,852,194 A | 12/1974 | Zine, Jr. |
| 3,862,042 A | 1/1975 | Ayres |
| 3,879,295 A | 4/1975 | Glover et al. |
| 3,882,021 A | 5/1975 | Ayres |
| 3,886,928 A | 6/1975 | Sarstedt |
| 3,887,464 A | 6/1975 | Ayres |
| 3,887,465 A | 6/1975 | Ayres |
| 3,887,466 A | 6/1975 | Ayres |
| 3,890,237 A | 6/1975 | Welch |
| 3,890,954 A | 6/1975 | Greenspan |
| 3,891,553 A | 6/1975 | Ayres |
| 3,894,950 A | 7/1975 | Ayres et al. |
| 3,894,951 A | 7/1975 | Ayres |
| 3,894,952 A | 7/1975 | Ayres |
| 3,897,337 A | 7/1975 | Ayres |
| 3,897,340 A | 7/1975 | Ayres |
| 3,897,343 A | 7/1975 | Ayres |
| 3,901,219 A | 8/1975 | Kay |
| 3,909,419 A | 9/1975 | Ayres |
| 3,919,085 A | 11/1975 | Ayres |
| 3,920,549 A | 11/1975 | Gigliello et al. |
| 3,920,557 A | 11/1975 | Ayres |
| 3,929,646 A | 12/1975 | Adler |
| 3,931,018 A | 1/1976 | North, Jr. |
| 3,932,277 A | 1/1976 | McDermott et al. |
| 3,935,113 A | 1/1976 | Ayres |
| 3,941,699 A | 3/1976 | Ayres |
| 3,945,928 A | 3/1976 | Ayres |
| 3,947,176 A | 3/1976 | Rainville |
| 3,951,801 A | 4/1976 | Ayres |
| 3,957,654 A | 5/1976 | Ayres |
| 3,960,727 A | 6/1976 | Hochstrasser |
| 3,969,250 A | 7/1976 | Farr |
| 3,970,565 A | 7/1976 | Ahlstrand et al. |
| 3,972,812 A | 8/1976 | Gresl, Jr. |
| 3,981,804 A | 9/1976 | Gigliello |
| 4,001,122 A | 1/1977 | Griffin |
| 4,004,868 A | 1/1977 | Ohdate |
| 4,021,340 A | 5/1977 | Zine, Jr. |
| 4,021,352 A | 5/1977 | Sarstedt |
| 4,027,660 A | 6/1977 | Wardlaw et al. |
| 4,055,501 A | 10/1977 | Cornell |
| 4,057,499 A | 11/1977 | Buono |
| 4,077,396 A | 3/1978 | Wardlaw et al. |
| 4,082,085 A | 4/1978 | Wardlaw et al. |
| 4,083,788 A | 4/1978 | Ferrara |
| 4,088,582 A | 5/1978 | Murty et al. |
| 4,119,125 A | 10/1978 | Elkins |
| 4,131,549 A | 12/1978 | Ferrara |
| 4,134,832 A | 1/1979 | Heimreid |
| 4,142,668 A | 3/1979 | Lee |
| 4,152,270 A | 5/1979 | Cornell |
| 4,154,690 A | 5/1979 | Ballies |
| 4,159,896 A | 7/1979 | Levine et al. |
| 4,169,060 A | 9/1979 | Columbus |
| 4,189,385 A | 2/1980 | Greenspan |
| 4,201,209 A | 5/1980 | LeVeen et al. |
| 4,202,769 A | 5/1980 | Greenspan |
| 4,243,362 A | 1/1981 | Rees et al. |
| 4,246,123 A | 1/1981 | Cornell et al. |
| 4,257,886 A | 3/1981 | Kessler |
| 4,275,030 A | 6/1981 | Mares |
| 4,279,863 A | 7/1981 | Friehler |
| 4,294,707 A | 10/1981 | Ikeda et al. |
| 4,315,892 A | 2/1982 | Stone et al. |
| 4,364,832 A | 12/1982 | Ballies |
| 4,369,117 A | 1/1983 | White |
| 4,379,849 A | 4/1983 | Heimreid |
| 4,381,275 A | 4/1983 | Sorensen |
| 4,396,381 A | 8/1983 | Fanger et al. |
| 4,409,988 A | 10/1983 | Greenspan |
| 4,417,981 A | 11/1983 | Nugent |
| 4,425,235 A | 1/1984 | Cornell et al. |
| 4,426,290 A | 1/1984 | Ichikawa et al. |
| 4,443,345 A | 4/1984 | Wells |
| 4,444,711 A | 4/1984 | Schad |
| 4,448,741 A | 5/1984 | Schad |
| 4,464,254 A | 8/1984 | Dojki et al. |
| 4,470,936 A | 9/1984 | Potter |
| 4,492,634 A | 1/1985 | Villa-Real |
| 4,508,676 A | 4/1985 | Sorensen |
| 4,517,090 A | 5/1985 | Kersten et al. |
| 4,522,713 A | 6/1985 | Nussbaumer et al. |
| 4,533,474 A | 8/1985 | Arnaudeau |
| 4,535,014 A | 8/1985 | Wright |
| 4,567,754 A | 2/1986 | Wardlaw et al. |
| 4,569,764 A | 2/1986 | Satchell |
| 4,602,995 A | 7/1986 | Cassaday et al. |
| 4,701,292 A | 10/1987 | Valyi |
| 4,707,276 A | 11/1987 | Dodge et al. |
| 4,717,324 A | 1/1988 | Schad et al. |
| 4,726,758 A | 2/1988 | Sekine et al. |
| 4,770,779 A | 9/1988 | Ichikawa et al. |
| 4,803,031 A | 2/1989 | Ochs et al. |
| 4,818,386 A | 4/1989 | Burns |
| 4,828,716 A | 5/1989 | McEwen et al. |
| 4,832,851 A | 5/1989 | Bowers et al. |
| 4,843,869 A | 7/1989 | Levine et al. |
| 4,853,137 A | 8/1989 | Ersson |
| 4,877,520 A | 10/1989 | Burns |
| 4,917,801 A | 4/1990 | Luderer et al. |
| 4,935,184 A | 6/1990 | Sorensen |
| 4,957,637 A | 9/1990 | Cornell |
| 4,957,682 A | 9/1990 | Kobayashi et al. |
| 5,007,892 A | 4/1991 | Columbus |
| 5,019,243 A | 5/1991 | McEwen et al. |
| 5,028,226 A | 7/1991 | De'ath et al. |
| 5,030,341 A | 7/1991 | McEwen et al. |
| 5,086,784 A | 2/1992 | Levine et al. |
| 5,112,490 A | 5/1992 | Turpen |
| 5,171,533 A | 12/1992 | Fine et al. |
| 5,236,604 A | 8/1993 | Fiehler |
| 5,251,474 A | 10/1993 | Wardlaw et al. |
| 5,269,927 A | 12/1993 | Fiehler |
| 5,271,852 A | 12/1993 | Luoma, II |
| 5,282,981 A | 2/1994 | Adams et al. |
| 5,308,506 A | 5/1994 | McEwen et al. |
| 5,325,977 A | 7/1994 | Haynes et al. |
| 5,354,483 A | 10/1994 | Furse |
| 5,389,265 A | 2/1995 | Luoma, II |
| 5,393,494 A | 2/1995 | Greenfield et al. |
| 5,419,835 A | 5/1995 | Adams et al. |
| 5,422,018 A | 6/1995 | Saunders et al. |
| 5,454,958 A | 10/1995 | Fiehler |
| 5,455,009 A | 10/1995 | Vogler et al. |
| 5,456,885 A | 10/1995 | Coleman et al. |
| 5,462,716 A | 10/1995 | Holm |
| 5,474,687 A | 12/1995 | Van Vlasselaer |
| 5,511,558 A | 4/1996 | Shepard et al. |
| 5,533,518 A | 7/1996 | Vogler |
| 5,552,325 A | 9/1996 | Nochumson et al. |
| 5,556,541 A | 9/1996 | Ruschke |
| 5,560,830 A | 10/1996 | Coleman et al. |
| 5,575,778 A | 11/1996 | Hardt et al. |
| 5,577,513 A | 11/1996 | Van Vlasselaer |
| 5,632,895 A | 5/1997 | Tsukagoshi et al. |
| 5,632,905 A | 5/1997 | Haynes |

(56) References Cited

U.S. PATENT DOCUMENTS

| | | |
|---|---|---|
| 5,646,004 A | 7/1997 | Van Vlasselaer |
| 5,648,223 A | 7/1997 | Van Vlasselaer |
| 5,651,998 A | 7/1997 | Bertschi et al. |
| 5,707,876 A | 1/1998 | Levine |
| 5,736,033 A | 4/1998 | Coleman et al. |
| 5,755,360 A | 5/1998 | Elliott |
| 5,785,925 A | 7/1998 | U'Ren |
| 5,789,033 A | 8/1998 | Bertschi et al. |
| 5,798,069 A | 8/1998 | Bertschi et al. |
| 5,840,502 A | 11/1998 | Van Vlasselaer |
| 5,853,600 A | 12/1998 | McNeal et al. |
| 5,860,937 A | 1/1999 | Cohen |
| 5,902,276 A | 5/1999 | Namey, Jr. |
| 5,955,009 A | 9/1999 | Kazuma |
| 6,001,087 A | 12/1999 | Zurcher |
| 6,074,613 A | 6/2000 | Harness et al. |
| 6,074,883 A | 6/2000 | Kelly et al. |
| 6,106,261 A | 8/2000 | von Holdt |
| 6,161,712 A | 12/2000 | Savitz et al. |
| 6,174,447 B1 | 1/2001 | Spindler |
| 6,225,123 B1 | 5/2001 | Cohen et al. |
| 6,277,331 B1 | 8/2001 | Konrad |
| 6,280,400 B1 | 8/2001 | Niermann |
| 6,296,796 B1 | 10/2001 | Gordon |
| 6,302,919 B1 | 10/2001 | Chambers et al. |
| 6,379,139 B1 | 4/2002 | Boucherie |
| 6,390,966 B2 | 5/2002 | Anderson |
| 6,406,671 B1 | 6/2002 | DiCesare et al. |
| 6,409,528 B1 | 6/2002 | Bodnar |
| 6,464,921 B1 | 10/2002 | Armbruster |
| 6,465,256 B1 | 10/2002 | Iskra |
| 6,471,069 B2 | 10/2002 | Lin et al. |
| 6,479,298 B1 | 11/2002 | Miller et al. |
| 6,497,325 B1 | 12/2002 | Karg et al. |
| 6,516,953 B1 | 2/2003 | DiCesare et al. |
| 6,537,503 B1 | 3/2003 | Conway |
| 6,558,149 B1 | 5/2003 | Bodmer et al. |
| 6,582,904 B2 | 6/2003 | Dahm |
| 6,593,145 B2 | 7/2003 | Macfarlane et al. |
| 6,607,685 B2 | 8/2003 | Naritomi et al. |
| 6,623,688 B2 | 9/2003 | Gedritis et al. |
| 6,740,240 B2 | 5/2004 | Coville et al. |
| 6,758,804 B2 | 7/2004 | Anderson |
| 6,783,346 B2 | 8/2004 | Bodmer et al. |
| 6,793,892 B1 | 9/2004 | Niermann |
| 6,803,022 B2 | 10/2004 | DiCesare et al. |
| 6,817,256 B2 | 11/2004 | Mehra et al. |
| 6,866,811 B2 | 3/2005 | Kayano et al. |
| 6,933,148 B2 | 8/2005 | Collins et al. |
| 6,976,509 B1 | 12/2005 | Kirvan |
| 6,979,307 B2 | 12/2005 | Beretta et al. |
| 7,074,577 B2 | 7/2006 | Haubert et al. |
| 7,077,273 B2 | 7/2006 | Ellsworth et al. |
| 7,153,477 B2 | 12/2006 | DiCesare et al. |
| 7,158,854 B1 | 1/2007 | Kolander |
| 7,166,218 B2 | 1/2007 | Trapy et al. |
| 7,179,391 B2 | 2/2007 | Leach et al. |
| 7,188,734 B2 | 3/2007 | Konrad |
| 7,205,157 B2 | 4/2007 | Jurgensen et al. |
| 7,211,433 B1 | 5/2007 | Dahm et al |
| 7,220,593 B2 | 5/2007 | Haubert et al. |
| 7,223,346 B2 | 5/2007 | Dorian et al. |
| 7,282,168 B2 | 10/2007 | Downer et al. |
| 7,294,311 B2 | 11/2007 | Coville |
| 7,309,468 B2 | 12/2007 | Stevens et al. |
| 7,329,534 B2 | 2/2008 | Haubert et al. |
| 7,358,095 B2 | 4/2008 | Haubert et al. |
| 7,374,678 B2 | 5/2008 | Leach et al. |
| 7,445,125 B2 | 11/2008 | Ellsworth et al. |
| 7,470,371 B2 | 12/2008 | Dorian et al. |
| 7,547,272 B2 | 6/2009 | Ellsworth et al. |
| 7,578,975 B2 | 8/2009 | DiCesare et al. |
| 7,629,176 B2 | 12/2009 | Haubert et al. |
| 7,645,425 B2 | 1/2010 | Haywood et al. |
| 7,736,593 B2 | 6/2010 | Dastane et al. |
| 7,745,106 B2 | 6/2010 | Beretta et al. |
| 7,767,087 B2 | 8/2010 | Wilson |
| 7,771,590 B2 | 8/2010 | Leach et al. |
| 7,780,860 B2 | 8/2010 | Higgins et al. |
| 7,806,276 B2 | 10/2010 | Leach et al. |
| 7,832,566 B2 | 11/2010 | Leach et al. |
| 7,837,884 B2 | 11/2010 | Dorian et al. |
| 7,845,499 B2 | 12/2010 | Higgins et al. |
| 7,901,584 B2 | 3/2011 | Dorian et al. |
| 7,914,689 B2 | 3/2011 | Higgins et al. |
| 7,915,029 B2 | 3/2011 | Haubert et al. |
| 7,919,049 B2 | 4/2011 | Haubert et al. |
| 7,922,972 B2 | 4/2011 | Ellsworth et al. |
| 7,927,563 B1 | 4/2011 | Lavi |
| 7,947,186 B2 | 5/2011 | Soares et al. |
| 7,947,236 B2 | 5/2011 | Losada et al. |
| 7,954,646 B2 | 6/2011 | Leach et al. |
| 7,955,501 B2 | 6/2011 | Wilson |
| 7,972,578 B2 | 7/2011 | DiCesare et al. |
| 7,992,725 B2 | 8/2011 | Leach et al. |
| 8,012,077 B2 | 9/2011 | Hoeppner |
| 8,012,742 B2 | 9/2011 | Haubert et al. |
| 8,048,297 B2 | 11/2011 | Leach et al. |
| 8,048,320 B2 | 11/2011 | Leach et al. |
| 8,048,321 B2 | 11/2011 | Leach et al. |
| 8,062,534 B2 | 11/2011 | Higgins et al. |
| 8,092,692 B2 | 1/2012 | Nilsen et al. |
| 8,114,680 B2 | 2/2012 | Haubert et al. |
| 8,119,013 B2 | 2/2012 | Leach et al. |
| 8,133,389 B2 | 3/2012 | Dorian et al. |
| 8,206,648 B2 | 6/2012 | Sattler |
| RE43,547 E | 7/2012 | Ellsworth et al. |
| 8,236,258 B2 | 8/2012 | Leach et al. |
| 8,241,592 B2 | 8/2012 | Duffy, Jr. et al. |
| 8,282,839 B2 | 10/2012 | Ellsworth |
| 8,313,954 B2 | 11/2012 | Leach et al. |
| 8,348,066 B2 | 1/2013 | Ellsworth |
| 8,394,342 B2 | 3/2013 | Felix et al. |
| 8,474,630 B2 | 7/2013 | Dorian et al. |
| 8,518,272 B2 | 8/2013 | Hoeppner |
| 8,801,586 B2 | 8/2014 | Dorian et al. |
| 9,162,232 B2 | 10/2015 | Ellsworth |
| 2002/0023884 A1 | 2/2002 | Anderson |
| 2002/0094305 A1 | 7/2002 | Dicesare et al. |
| 2002/0098137 A1 | 7/2002 | Hommeltoft |
| 2002/0132367 A1 | 9/2002 | Miller et al. |
| 2002/0156439 A1 | 10/2002 | Iskra |
| 2002/0185778 A1 | 12/2002 | Armbruster |
| 2003/0028154 A1 | 2/2003 | Ross |
| 2003/0039717 A1 | 2/2003 | Hwang et al. |
| 2003/0205538 A1 | 11/2003 | Dorian et al. |
| 2004/0013575 A1 | 1/2004 | Stevens et al. |
| 2004/0043505 A1 | 3/2004 | Walenciak et al. |
| 2004/0059255 A1 | 3/2004 | Manoussakis et al. |
| 2004/0129631 A1 | 7/2004 | Anraku et al. |
| 2004/0149287 A1 | 8/2004 | Namey, Jr. |
| 2004/0166029 A1 | 8/2004 | Losada et al. |
| 2004/0210196 A1 | 10/2004 | Bush, Jr. et al. |
| 2004/0241364 A1 | 12/2004 | Zihlmann |
| 2004/0256331 A1 | 12/2004 | Arking et al. |
| 2005/0033237 A1 | 2/2005 | Fentress et al. |
| 2005/0037165 A1 | 2/2005 | Ahern et al. |
| 2005/0059163 A1 | 3/2005 | Dastane et al. |
| 2005/0124965 A1 | 6/2005 | Haywood |
| 2005/0170114 A1 | 8/2005 | Hill |
| 2005/0186120 A1 | 8/2005 | Dorian et al. |
| 2005/0261620 A1 | 11/2005 | Ballin |
| 2006/0032825 A1 | 2/2006 | Ellsworth et al. |
| 2006/0036231 A1 | 2/2006 | Conard et al. |
| 2006/0068206 A1 | 3/2006 | Hala et al. |
| 2006/0089602 A1 | 4/2006 | Boucherie |
| 2006/0116270 A1 | 6/2006 | Hatamian et al. |
| 2006/0212020 A1 | 9/2006 | Rainen et al. |
| 2006/0263266 A1 | 11/2006 | DiCesare et al. |
| 2006/0278588 A1 | 12/2006 | Woodell-May |
| 2007/0020629 A1 | 1/2007 | Ross et al. |
| 2007/0034579 A1 | 2/2007 | Dorian et al. |
| 2007/0096364 A1 | 5/2007 | Hahn et al. |
| 2007/0102344 A1 | 5/2007 | Konrad |

(56) References Cited

U.S. PATENT DOCUMENTS

| | | |
|---|---|---|
| 2007/0191775 A1 | 8/2007 | Diep et al. |
| 2007/0267776 A1 | 11/2007 | Conard et al. |
| 2008/0023414 A1 | 1/2008 | Konrad |
| 2008/0290048 A1 | 11/2008 | Jaeggi et al. |
| 2010/0120596 A1 | 5/2010 | Froman et al. |
| 2010/0155343 A1 | 6/2010 | Battles et al. |
| 2010/0160135 A1 | 6/2010 | Bartfeld et al. |
| 2010/0288694 A1 | 11/2010 | Crawford et al. |
| 2011/0014705 A1 | 1/2011 | Leach et al. |
| 2011/0100919 A1 | 5/2011 | Dorian et al. |
| 2011/0266206 A1 | 11/2011 | Coleman |
| 2012/0015796 A1 | 1/2012 | Leach et al. |
| 2012/0045424 A1 | 2/2012 | Esteron |
| 2012/0129676 A1 | 5/2012 | Duffy et al. |
| 2013/0017130 A1 | 1/2013 | Haubert |
| 2013/0095007 A1 | 4/2013 | Haubert et al. |
| 2015/0231626 A1 | 8/2015 | Shi et al. |

FOREIGN PATENT DOCUMENTS

| | | |
|---|---|---|
| DE | 19513453 C2 | 3/1997 |
| DE | 102010000645 A1 | 9/2011 |
| EP | 0017127 B1 | 10/1980 |
| EP | 0056609 B1 | 7/1982 |
| EP | 0119692 B1 | 9/1984 |
| EP | 0137292 B1 | 3/1990 |
| EP | 0392377 A2 | 10/1990 |
| EP | 0184274 B1 | 5/1992 |
| EP | 0385953 B1 | 4/1993 |
| EP | 0537507 A1 | 4/1993 |
| EP | 0399151 B1 | 8/1994 |
| EP | 0638804 A1 | 2/1995 |
| EP | 0520184 B1 | 1/1996 |
| EP | 0520185 B1 | 2/1996 |
| EP | 0638171 B1 | 6/1996 |
| EP | 0753741 A1 | 1/1997 |
| EP | 0494079 B1 | 3/1997 |
| EP | 0766973 A1 | 4/1997 |
| EP | 0493838 B1 | 5/1997 |
| EP | 0627261 B1 | 5/1998 |
| EP | 0640215 B1 | 11/1998 |
| EP | 0817680 B1 | 12/1999 |
| EP | 0678557 B1 | 6/2000 |
| EP | 1005910 A2 | 6/2000 |
| EP | 1016460 A2 | 7/2000 |
| EP | 0688606 B1 | 12/2000 |
| EP | 1106252 A2 | 6/2001 |
| EP | 0739229 B1 | 10/2001 |
| EP | 0744026 B1 | 11/2001 |
| EP | 1205250 A1 | 5/2002 |
| EP | 1221342 A2 | 7/2002 |
| EP | 0875757 B1 | 6/2003 |
| EP | 0928301 B1 | 1/2004 |
| EP | 1005909 B1 | 5/2004 |
| EP | 1107002 B1 | 8/2004 |
| EP | 1192996 B1 | 8/2004 |
| EP | 1106250 B1 | 4/2005 |
| EP | 1106251 B1 | 11/2005 |
| EP | 1106253 B1 | 11/2005 |
| EP | 1014088 B1 | 3/2006 |
| EP | 1006360 B1 | 5/2006 |
| EP | 1693109 A1 | 8/2006 |
| EP | 1189967 B1 | 3/2007 |
| EP | 1772191 A1 | 4/2007 |
| EP | 1509326 B1 | 6/2007 |
| EP | 1289618 B1 | 1/2008 |
| GB | 2293986 A | 4/1996 |
| JP | 3270701 A | 12/1991 |
| JP | 581712 U | 11/1993 |
| JP | 9292393 A | 11/1997 |
| JP | 2000199760 A | 7/2000 |
| JP | 2003185653 A | 7/2003 |
| RU | 2062465 C1 | 6/1996 |
| WO | 9322673 A1 | 11/1993 |
| WO | 9520675 A1 | 8/1995 |
| WO | 9605770 A1 | 2/1996 |
| WO | 9607097 A1 | 3/1996 |
| WO | 9609308 A1 | 3/1996 |
| WO | 9712679 A1 | 4/1997 |
| WO | 9851411 A2 | 11/1998 |
| WO | 0114850 A1 | 3/2001 |
| WO | 0181002 A1 | 11/2001 |
| WO | 0209840 A1 | 2/2002 |
| WO | 02073190 A1 | 9/2002 |
| WO | 03035888 A1 | 5/2003 |
| WO | 03099412 A1 | 12/2003 |
| WO | 2004030826 A2 | 4/2004 |
| WO | 2004031770 A1 | 4/2004 |
| WO | 2005014173 A1 | 2/2005 |
| WO | 2005080965 A1 | 9/2005 |
| WO | 2006104636 A1 | 10/2006 |
| WO | 2006121728 A2 | 11/2006 |
| WO | 2006135856 A2 | 12/2006 |
| WO | 2007000986 A1 | 1/2007 |
| WO | 2007095450 A2 | 8/2007 |
| WO | 2008038012 A1 | 4/2008 |
| WO | 2008049359 A1 | 5/2008 |
| WO | 2008097091 A1 | 8/2008 |
| WO | 2008114998 A1 | 9/2008 |
| WO | 2008127639 A1 | 10/2008 |
| WO | 2009021257 A1 | 2/2009 |
| WO | 2011069145 A2 | 6/2011 |
| WO | 2011126867 A1 | 10/2011 |
| WO | 2012003873 A1 | 1/2012 |
| WO | 2014039498 A1 | 3/2014 |

MECHANICAL SEPARATOR FOR A BIOLOGICAL FLUID

CROSS-REFERENCE TO RELATED APPLICATION

The present application claims priority to U.S. Provisional Patent Application No. 62/079,216, entitled "Mechanical Separator for a Biological Fluid" filed Nov. 13, 2014, the entire disclosure of which is hereby incorporated by reference.

BACKGROUND OF THE INVENTION

Field of the Invention

The subject invention relates to a device for separating higher and lower density fractions of a fluid sample. More particularly, this invention relates to a device for collecting and transporting fluid samples whereby the device and fluid sample are subjected to centrifugation in order to cause separation of the higher density fraction from the lower density fraction of the fluid sample.

Description of Related Art

Diagnostic tests may require separation of a patient's whole blood sample into components, such as serum or plasma (the lower density phase components), and red blood cells (the higher density phase components). Samples of whole blood are typically collected by venipuncture through a cannula or needle attached to a syringe or an evacuated blood collection tube. After collection, separation of the blood into serum or plasma and red blood cells is accomplished by rotation of the syringe or tube in a centrifuge. In order to maintain the separation, a barrier must be positioned between the higher density and lower density phase components. This allows the separated components to be subsequently examined.

A variety of separation barriers have been used in collection devices to divide the area between the higher density and lower density phases of a fluid sample. The most widely used devices include thixotropic gel materials, such as polyester gels. However, current polyester gel serum separation tubes require special manufacturing equipment to both prepare the gel and fill the tubes. Moreover, the shelf-life of the gel-based separator product is limited. Over time, globules may be released from the gel mass and enter one or both of the separated phase components. Furthermore, commercially available gel barriers may react chemically with the analytes. Accordingly, if certain drugs are present in the blood sample when it is taken, an adverse chemical reaction with the gel interface can occur. Furthermore, if an instrument probe is inserted too deeply into a collection container, then the instrument probe may become clogged if it contacts the gel.

Certain mechanical separators have also been proposed in which a mechanical barrier can be employed between the higher and lower density phases of the fluid sample. Conventional mechanical barriers are positioned between higher and lower density phase components utilizing elevated gravitational forces applied during centrifugation. For proper orientation with respect to plasma and serum specimens, conventional mechanical separators are typically positioned above the collected whole blood specimen prior to centrifugation. This typically requires that the mechanical separator be affixed to the underside of the tube closure in such a manner that blood fill occurs through or around the device when engaged with a blood collection set or phlebotomy needle. This attachment is required to prevent the premature movement of the separator during shipment, handling, and blood draw. Conventional mechanical separators are typically affixed to the tube closure by a mechanical interlock between the bellows component and the closure.

Conventional mechanical separators have some significant drawbacks. As shown in FIG. 1, conventional separators include a bellows 2 for providing a seal with a tube or syringe wall 4. Typically, at least a portion of the bellows 2 is housed within, or in contact with, a closure 6. As shown in FIG. 1, as a needle 8 enters through the closure 6, the bellows 2 is depressed. This creates a void 9 in which blood may pool during insertion or removal of the needle. This can result in sample pooling under the closure, device pre-launch in which the mechanical separator prematurely releases during blood collection, trapping of a significant quantity of fluid phases, such as serum and plasma, poor sample quality, and/or barrier failure under certain circumstances. Furthermore, previous mechanical separators are costly and complicated to manufacture due to the complicated multi-part fabrication techniques.

In addition, it is desired to reduce damage to the cellular structure of the fluid which can occur when the fluid or a portion of the fluid is trapped between the separator and the collection tube resulting in a shearing force being placed on the fluid.

Accordingly, a need exists for a separator device that is compatible with standard sampling equipment and reduces or eliminates the aforementioned problems of conventional separators. A need also exists for a separator device that is easily used to separate a blood sample, minimizes cross-contamination of the higher and lower density phases of the sample during centrifugation, is independent of temperature during storage and shipping, and is stable to radiation sterilization. A need further exists for a unitary separation device that requires fewer relative moving parts and that allows for enhanced ease of introducing a specimen into a collection container.

SUMMARY OF THE INVENTION

In accordance with an aspect of the present invention, a separation assembly for enabling separation of a fluid into first and second parts includes a container having a first end, a second end, and a sidewall extending therebetween having an inner surface and defining a container interior. The container defines a longitudinal axis between the first end and the second end. The separation assembly also includes a separator body disposed within the container interior and having a through-hole defined therethrough. The separator body includes a first part, and a second part interfaced with the first part. The separator body is transitionable from a first position in which the through-hole is provided in fluid-receiving alignment with the first end of the container, to a second position in which the through-hole is provided substantially perpendicular to the longitudinal axis of the container. In the first position, a through-axis of the through-hole of the separator body is in a plane that is not parallel with a plane containing the longitudinal axis of the container.

In certain configurations, the first part of the separator body is a float and the float defines an upper surface of the separator body and the second part of the separator body is a ballast and the ballast defines a lower surface of the separator body.

When the separator body is in the first position, the separator body may contact the sidewall of the container at a location that is offset from a center of the upper surface of the float. When the separator body is in the first position, the separator body may contact the sidewall of the container at a location that is offset from a center of the lower surface of the ballast. When in the second position, the separator body may contact the sidewall of the container at at least part of a periphery of the upper surface of the float, such as during centrifugation. When in the second position, the separator body may contact the sidewall of the container at the entire periphery of the upper surface of the float, such as after cessation of centrifugation.

In certain configurations, the first part of the separator body or a part of the first part of the separator body and a part of the second part of the separator body may define the through-hole.

In accordance with an aspect of the present invention, a separation assembly for enabling separation of a fluid into first and second parts includes a container having a first end, a second end, and a sidewall extending therebetween having an inner surface and defining a container interior. The container defines a longitudinal axis between the first end and the second end. The assembly also includes a separator body disposed within the container interior and having a through-hole defined therethrough. The separator body includes a first part, and a second part interfaced with the first part. The separator body is transitionable from a first position in which the through-hole is provided in fluid-receiving alignment with the first end of the container, to a second position in which the through-hole is provided substantially perpendicular to the longitudinal axis of the container. In the first position, a through-axis of the through-hole is angled with respect to at least one of the longitudinal axis of the container and the sidewall of the container.

In certain configurations, in the first position, the through-axis of the through-hole is angled from about 30° to about 60° with respect to the sidewall of the container. The first part of the separator body may be a float and the float may define an upper surface of the separator body, and the second part of the separator body may be a ballast and the ballast may define a lower surface of the separator body.

In certain configurations, when in the first position, the separator body may contact the sidewall of the container at a location that is offset from a center of the upper surface of the float. When in the first position, the separator body may contact the sidewall of the container at a location that is offset from a center of the lower surface of the ballast.

In still other configurations, a first part of the separator body, or a part of the first part of the separator body and a part of the second part of the separator body may define the through-hole. When in the second position, the separator body may contact the sidewall of the container at at least part of a periphery of the upper surface of the float, such as during centrifugation. When in the second position, the separator body may contact the sidewall of the container at the entire periphery of the upper surface of the float, such as after cessation of centrifugation.

In accordance with another aspect of the present invention, a separation assembly for enabling separation of a fluid into first and second parts includes a container having a first end, a second end, and a sidewall extending therebetween having an inner surface and defining a container interior. The container defines a longitudinal axis between the first end and the second end. The assembly also includes a separator body disposed within the container interior and having a through-hole for fluid to pass therethrough. The separator body includes a first part, and a second part interfaced with the first part. The separator body is transitionable from a first position in which the through-hole is provided in fluid-receiving alignment with the first end of the container, to a second position in which the through-hole is provided substantially perpendicular to the longitudinal axis of the container. In the first position, a through-axis of the through-hole of the separator is offset from the longitudinal axis of the container.

In certain configurations, the first part of the separator body is a float and the float defines an upper surface of the separator body, and the second part of the separator body is a ballast and the ballast defines a lower surface of the separator body. When in the first position, the separator body may contact the sidewall of the container at a location that is offset from a center of the upper surface of the float. When in the first position, the separator body may contact the sidewall of the container at a location that is offset from a center of the lower surface of the ballast.

In other configurations, the first part of the separator body or a part of the first part of the separator body and a part of the second part of the separator body may define the through-hole. When in the second position, the separator body may contact the sidewall of the container at at least part of a periphery of the upper surface of the float, such as during centrifugation. When in the second position, the separator body may contact the sidewall of the container at the entire periphery of the upper surface of the float, such as after cessation of centrifugation.

In accordance with another aspect of the present invention, a separation assembly for enabling separation of a fluid into first and second parts includes a container having a first end, a second end, and a sidewall extending therebetween having an inner surface and defining a container interior. The container defines a longitudinal axis between the first end and the second end. The separator body may be disposed within the container interior and may have a through-hole defined therethrough. The separator body includes a float and a ballast, with the float and the ballast being connected, and the float and the ballast both having leading parts, each defined by the float and the ballast end adjacent a second opening of the separator through-hole, and the float and ballast each having trailing parts, each defined by the float and ballast end adjacent the first opening of the separator through-hole. The separator body is transitionable from a first position in which the through-hole is provided in fluid-receiving alignment with the first end of the container, to a second position in which the through-hole is provided substantially perpendicular to the longitudinal axis of the container. In the first position, the trailing float part and the leading ballast part of the separator are provided adjacent the sidewall of the container and the leading float part and the trailing ballast part are spaced apart from the sidewall of the container.

DETAILED DESCRIPTION OF THE EMBODIMENTS

Figure 1:
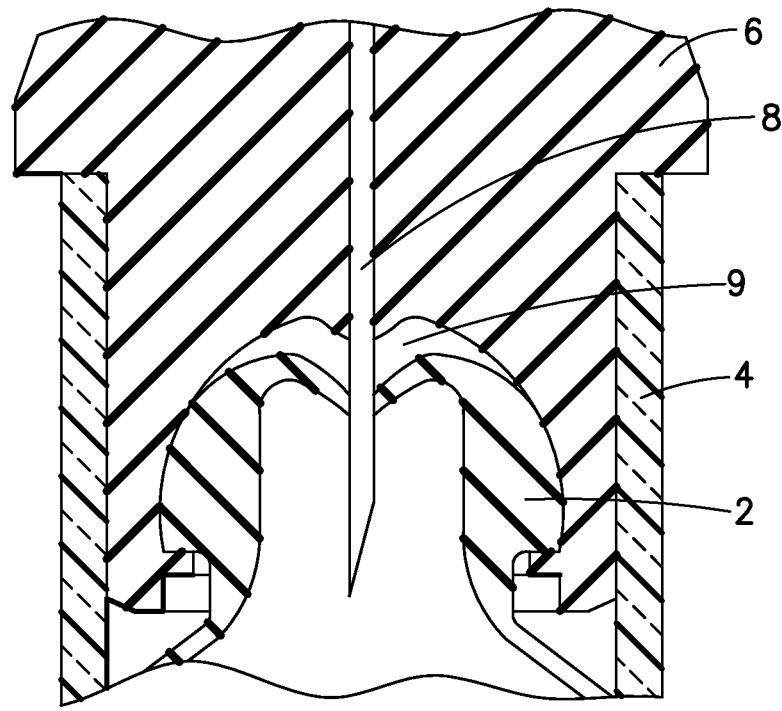
FIG. 1 is a partial cross-sectional side view of a conventional mechanical separator.
Figure 2:
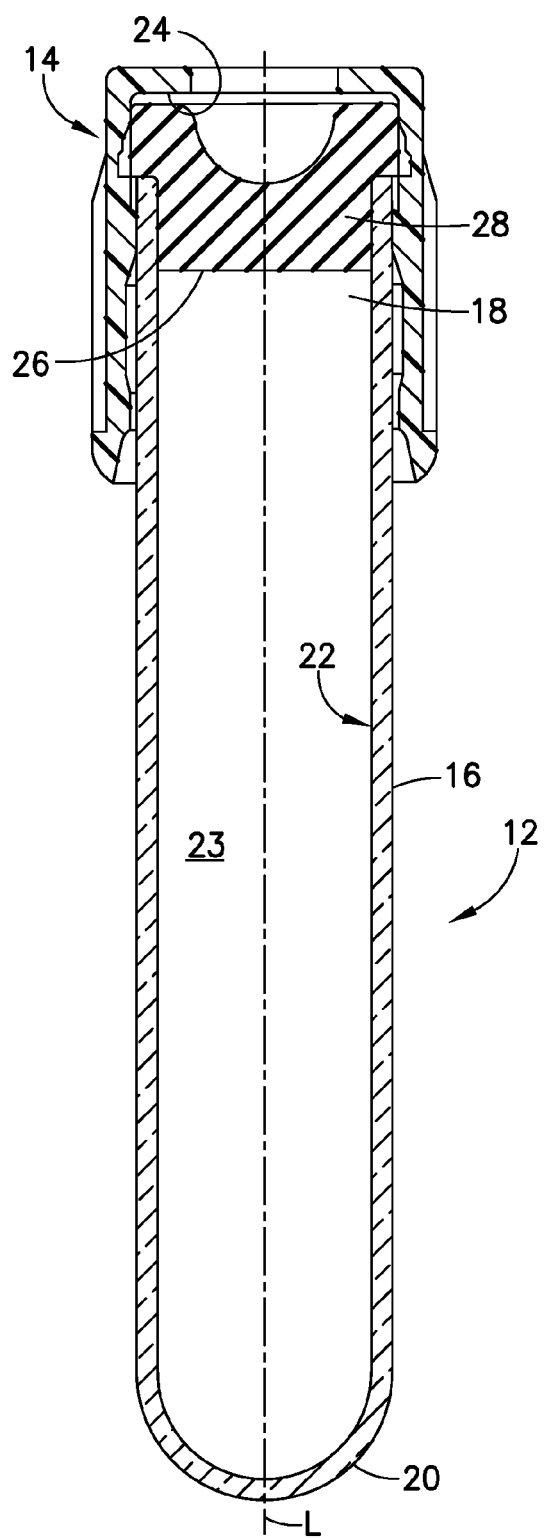
FIG. 2 is a cross-sectional view of a container in accordance with an embodiment of the present invention.
Figure 3:
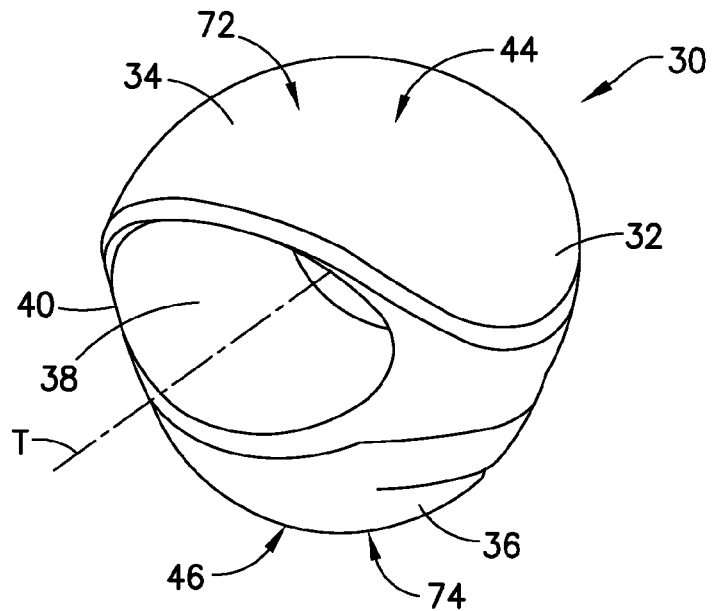
FIG. 3 is a perspective view of a mechanical separator in accordance with an embodiment of the present invention.

For purposes of the description hereinafter, the words "upper", "lower", "right", "left", "vertical", "horizontal", "top", "bottom", "lateral", "longitudinal", and like spatial terms, if used, shall relate to the described embodiments as oriented in the drawing figures. However, it is to be understood that many alternative variations and embodiments may be assumed except where expressly specified to the contrary. It is also to be understood that the specific devices and embodiments illustrated in the accompanying drawings and described herein are simply exemplary embodiments of the invention.

The separation assembly of the present invention is intended to provide separation of a sample into higher and lower density phase components, as will be discussed herein. For example, the present separation assembly can be used to provide a separation of serum or plasma from whole blood through the use of differential buoyancy to cause a sealing area to contract when submerged in a specimen exposed to elevated gravitational forces through applied rotational force or centrifugation. In one embodiment, the elevated gravitational forces can be provided at a rate of at least 2,000 revolutions/minute, such as at least 3,400 revolutions/minute.

As shown in FIGS. 2 and 8-10, a separation assembly 10 includes a container 12 having a closure 14. Specifically, the container 12 may be a sample collection tube, such as a proteomics, molecular diagnostics, chemistry sample tube, blood, or other bodily fluid collection tube, coagulation sample tube, hematology sample tube, and the like. Desirably, container 12 is an evacuated blood collection tube. The container 12 includes a first end 18, a second end 20, and a cylindrical sidewall 16 extending therebetween. The first end 18 may be an open top end and the second end 20 may be a closed bottom end. The cylindrical sidewall 16 includes an inner surface 22 and defines a container interior 23. The container 12 also defines a longitudinal axis L between the first end 18 and the second end 20 with an inside diameter extending substantially uniformly from the first end 18 to a location substantially adjacent the second end 20 along the longitudinal axis L of the container 12.

In one embodiment, the container 12 may contain additional additives as required for particular testing procedures, such as protease inhibitors, clotting agents, and the like. Such additives may be in particle or liquid form and may be sprayed onto the cylindrical sidewall 16 of the container 12 or located at the closed bottom second end 20 of the container 12.

The container 12 may be made of one or more than one of the following representative materials: polypropylene, polyethylene terephthalate (PET), glass, or combinations thereof. The container 12 can include a single wall or multiple wall configurations. Additionally, the container 12 may be constructed in any practical size for obtaining an appropriate biological sample. For example, the container 12 may be of a size similar to conventional large volume tubes, small volume tubes, or microliter volume tubes, as is known in the art. In one particular embodiment, the container 12 may be a standard 13 ml evacuated blood collection tube, as is also known in the art.

The open top first end 18 is structured to at least partially receive the closure 14 therein to form a liquid impermeable seal. The closure 14 includes a top end 24 and a bottom end 26 structured to be at least partially received within the container 12. Portions of the closure 14 adjacent the open top first end 18 of the container 12 define a maximum outer diameter which exceeds the inside diameter of the container 12. In one embodiment, the closure 14 includes a pierceable resealable septum 28 penetrable by a needle cannula (not shown). Portions of the closure 14 extending downwardly from the bottom end 26 may taper from a minor diameter which is approximately equal to, or slightly less than, the inside diameter of the container 12 to a major diameter that is greater than the inside diameter of the container 12 at the top end 24. Thus, the bottom end 26 of the closure 14 may be urged into a portion of the container 12 adjacent the open top first end 18. The inherent resiliency of closure 14 can insure a sealing engagement with the inner surface 22 of the cylindrical sidewall 16 of the container 12. In one embodiment, the closure 14 can be formed of a unitarily molded elastomeric material, having any suitable size and dimensions to provide sealing engagement with the container 12. Optionally, the closure 14 may be at least partially surrounded by a shield, such as a Hemogard® Shield commercially available from Becton, Dickinson and Company.

Referring to FIGS. 3-10, a mechanical separator 30 of the present invention includes a separator body 32 including a first part 34 and a second part 36 interfaced to the first part 34. The first part 34 has a first density and the second part 36 has a second density, with the second density being different from the first density and, preferably, greater than the first density. Alternatively or in addition, the first part 34 has a first buoyancy and the second part 36 has a second buoyancy, with the second buoyancy being different from the first buoyancy and, preferably, less than the first buoyancy.

One of the first part 34 or the second part 36 of the mechanical separator 30 may be extruded and/or molded of a resiliently deformable and self-sealable material, such as a thermoplastic elastomer (TPE). Alternatively, one of the first part 34 or the second part 36 of the mechanical separator 30 may be extruded and/or molded of a resiliently deformable material that exhibits good sealing characteristics when contact is established with the container 12, as will be discussed herein. Maintenance of the density within the specified tolerances is more easily obtained by using a standard material that does not require compounding with, for example, hollow glass micro-spheres in order to reduce the material density. The other of the first part 34 or the second part 36 of the mechanical separator 30 can be formed from mineral filled polypropylene.

One of the first part 34 or the second part 36 of the mechanical separator 30 is made from a material having a density that is less than the less dense phase of the liquid or specimen intended to be separated into two phases. For example, if it is desired to separate serum and plasma from human blood, then it is desirable that one of the first part 34 or the second part 36 have a density of no more than about 1.020 g/cc.

The other of the first part 34 or the second part 36 of the mechanical separator 30 is made from a material having a higher density than the more dense phase of the liquid or sample intended to be separated into two phases. For example, if it is desired to separate human blood into serum and plasma, then it is desirable that the other of the first part 34 or the second part 36 have a density of at least 1.105 g/cc. It is anticipated herein that both the first part 34 and the second part 36 may be formed of various other materials with sufficient biocompatibility, density stability, additive compatibility, and neutrality to analyte interactions, adsorption, and leachability.

The mechanical separator 30 also includes a through-hole 38 defined therein, such as along a through-axis T of the separator body 32. As shown in FIGS. 3 and 5-7, the through-hole 38 may extend through the entire separator body 32 and includes a first opening 40 and a second opening 42 aligned along the through-axis T. The through-hole 38 may bisect or substantially bisect the volumetric center of the separator body 32. The through-hole 38 may be defined by at least a portion of the first part 34 and at least a portion of the second part 36.

The first part 34 has an exterior surface 44 that is generally arcuate in shape, such as at least partially rounded or substantially rounded. The second part 36 also includes an exterior surface 46 that is also generally arcuate in shape, such as at least partially rounded or substantially rounded. When taken together, the exterior surface 44 of the first part 34 and the exterior surface 46 of the second part 36 form a generally round exterior. It is understood herein that the term "round exterior" includes configurations, in addition to a perfect sphere, that are aspects of the invention which may provide slightly non-uniform diameters taken through the mid-point. For example, different planes taken through the first part 34 and second part 36 which bisect the midpoint of the mechanical separator 30 may have varying diameters and still give rise to a generally rounded or ball-like mechanical separator 30.

Figure 5:
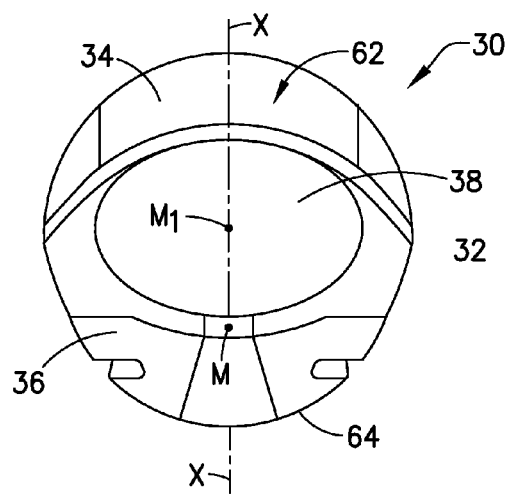
FIG. 5 is a front view of the mechanical separator of FIG. 3.

Due to the differential densities of the first part 34 and the second part 36, the mechanical separator 30 includes a center of mass M that is offset from the center of volume M1 of the separator body 32, as shown in FIG. 5. Specifically, the volume of the separator body 32 accounted for by the first part 34 may be significantly greater than the volume of the separator body 32 accounted for by the second part 36. Accordingly, the center of mass M of the separator body 32 may be offset from the center of the through-hole 38. Optionally, the center of volume M1 may also be offset from the center of the through-hole 38.

Figure 4:
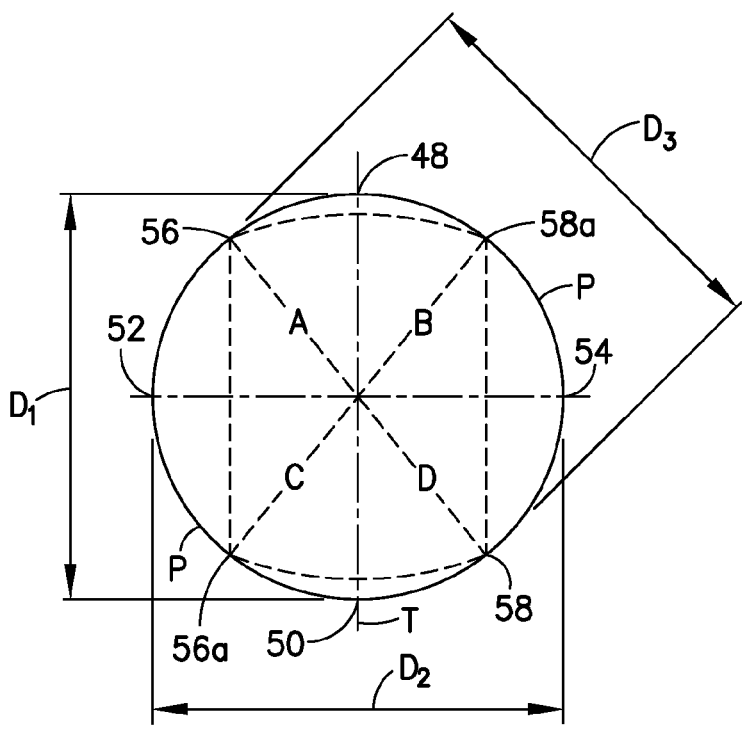
FIG. 4 is a top view of the mechanical separator of FIG. 3.
Figure 6:
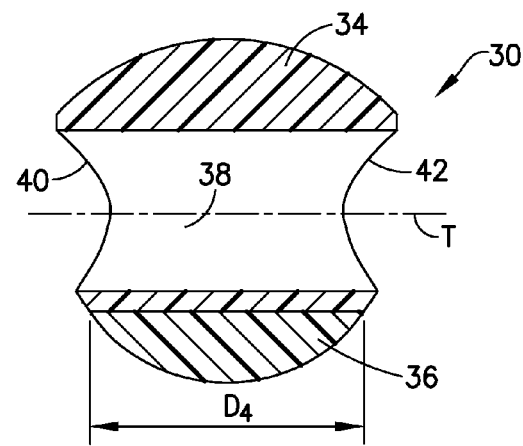
FIG. 6 is a cross-sectional view of the mechanical separator of FIG. 3 taken along the longitudinal axis X-X of the mechanical separator as shown in FIG. 5.

As shown in FIG. 4, the top profile of the separator body 32 may be non-circular. The diameter $D_1$ of the separator body 32, specifically the first part 34, taken across the first part 34 in the direction along the through-axis T of the through-hole 38 and extending between vertically outermost opposing tangent points 48, 50 of a perimeter P of the separator body 32 is less than the diameter $D_2$ of the separator body 32, specifically the first part 34, taken across the first part 34 in the direction perpendicular to the through-axis T of the through-hole 38 and extending between laterally outermost opposing tangent points 52, 54 of the perimeter P of the separator body 32. In addition, the diameter $D_3$ of the separator body 32, specifically the first part 34, taken across the first part 34 at an angle of substantially 45° to the through-axis T of the through-hole 38 and extending between diagonally outermost endpoints 56, 58 of the perimeter P of the separator body 32, may be larger than the diameter of the through-hole 38, and is greater than the diameters $D_1$ and $D_2$ of the separator body 32. The diameter $D_4$ of the second part 36 taken across the second part 36 along the through-axis T of the through-hole 38, as shown in FIG. 6, may be less than any of the diameters $D_1$, $D_2$, or $D_3$ of the separator body 32.

Referring to FIG. 4, a two-dimensional projection of the top profile of the first part 34 of the separator body 32 onto a plane may be symmetrical about an orientation plane extending between vertically outermost opposing tangent points 48, 50 of the perimeter P of the separator body 32 and from the top surface of the first part 34 to the bottom surface of the second part 36 and extending in the direction of the through-axis T of the through-hole 38. The two-dimensional projection of the top profile of the first part 34 of the separator body 32 onto a plane may also be symmetrical about an orientation plane extending between laterally outermost opposing tangent points 52, 54 of the perimeter P of the separator body 32 and from the top surface of the first part 34 to the bottom surface of the second part 36 and perpendicular to the direction of the through-axis T of the through-hole 38. A two-dimensional projection of the top profile of the first part 34 of the separator body 32 onto a plane may be asymmetrical about an orientation plane extending between diagonally outermost endpoints 56, 58 of the perimeter P of the separator body 32 and from the top surface of the first part 34 to the bottom surface of the second part 36 and in a direction diagonal to at least a part of the through-axis T of the through-hole 38. Accordingly, a two-dimensional projection of the top profile of the body 32 onto a plane may be asymmetric about an orientation plane extending between diagonally outermost endpoints 56a, 58a of the perimeter P of the separator body and from the top surface of the first part 34 to the bottom surface of the second part 36 and in a direction diagonal to at least a part of the through-axis T of the through-hole 38.

Further, the top profile of the separator body 32 defines a perimeter P that bounds four quadrants A, B, C, D, respectively defined by the intersection of a vertical axis extending between vertically outermost opposing tangent points 48, 50 of the perimeter P of the separator body 32 and a lateral axis extending between laterally outermost opposing tangent points 52, 54 of the perimeter P of the separator body 32. Each quadrant A, B, C, D is substantially bisected by an orientation axis extending between diagonally outermost endpoints 56, 58 or 56a, 58a of the perimeter P of the separator body 32 and bounded by the perimeter P of the separator body 32 as shown in FIG. 4. A two-dimensional projection of the top profile of the separator body 32 onto a plane may be symmetrical about $D_1$ and $D_2$ but may be asymmetrical with respect to $D_3$.

Figure 7:
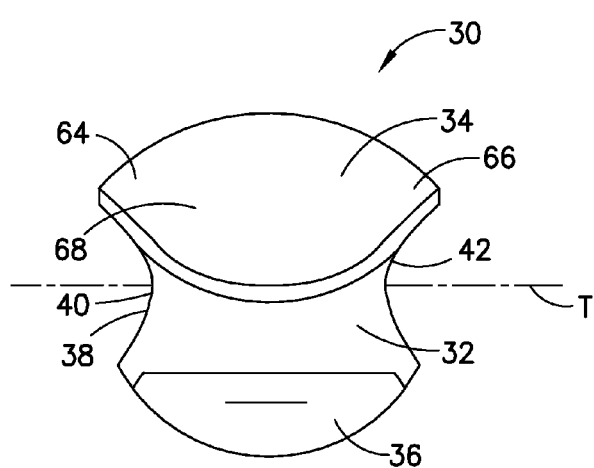
FIG. 7 is a side view of the mechanical separator of FIG. 3.

Thus, the top surface of the first part 34 includes a first extended part 64 adjacent the first opening 40 of the through-hole 38 defined by tangent point 48, endpoint 56, and endpoint 58a and a second extended part 66 adjacent the second opening 42 of the through-hole 38 defined by tangent point 50, endpoint 56a, and endpoint 58, that taken with an upper part 68 of the first part 34, form a substantially non-circular convex top surface of the first part 34 (FIG. 7).

Figure 8:
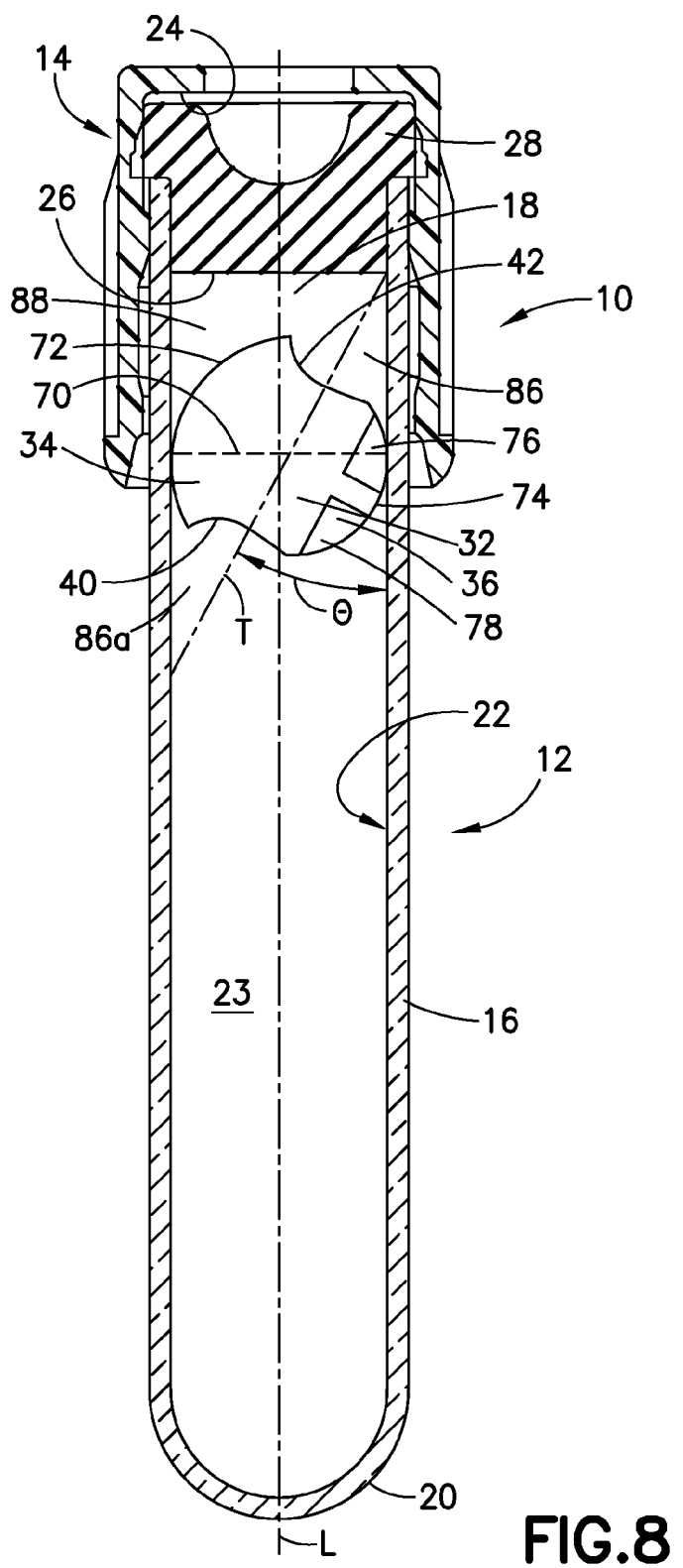
FIG. 8 is a partial cross-sectional front view of a separation assembly wherein the mechanical separator disposed within the container is in the first position for allowing fluid to pass through the through-hole in accordance with an embodiment of the present invention.

As shown in FIG. 8, in a first position, the mechanical separator 30 of the present invention is oriented within the container 12 in an initial position in which the through-axis T of the through-hole 38 of the mechanical separator 30 is in a plane that is not parallel to a plane containing the longitudinal axis L of the container 12. In this initial position, the through-hole 38 is adapted for allowing fluid to pass therethrough, such as from a needle cannula (not shown) which has pierced the pierceable septum 28 of the closure 14 and is provided in fluid communication with the interior 23 of the collection container 12. Further, since the through-axis T of the through-hole 38 of the mechanical separator 30 is offset with respect to the longitudinal axis L of the container 12, the second opening 42 of the through-hole 38 is located in close proximity to and adjacent the sidewall 16 of the longitudinal axis L of the container 12. This causes the fluid in this area to pass through the through-hole 38 and minimizes pooling of the fluid above and below the mechanical separator 30. This helps to reduce cellular damage to the fluid that can occur due to pooling of the fluid above the mechanical separator 30 as will be explained later.

In the first position, the through-axis T of the through-hole 38 is angled with respect to at least one of the longitudinal axis L of the container 12 and the sidewall 16 of the container 12. The angle θ of the through-axis T of the through-hole 38 with respect to the sidewall 16 of the container 12 may be from about 30° to about 60°.

Also, in the first position, the through-axis T of the through-hole 38 may be offset from the longitudinal axis L of the container 12.

In one embodiment, the first part 34 may be a float and the second part 36 may be a ballast where the second part 36 has a second density that is greater than a first density of the first part 34. The float 34 defines an upper surface 72 of the separator body 32 and the ballast 36 defines a lower surface 74 of the separator body 32. In this embodiment, when the mechanical separator 30 is in the first position, the separator body 32 contacts the sidewall 16 of the container 12 at a location that is offset from a center of the upper surface 72 of the float 34, and the separator body 32 contacts the sidewall 16 of the container 12 at a location that is offset from a center of the lower surface 74 of the ballast 36.

In this embodiment, in the first position, a leading ballast portion 76 of the separator body 32 is provided adjacent the sidewall 16 of the container 12 and a trailing ballast portion 78 is spaced apart from the sidewall 16 of the container 12.

In this position, a periphery 70 of the mechanical separator 30 forms an interference engagement with the sidewall 16 of the container 12 as shown in FIG. 8. In one configuration, the interference engagement may also form a seal with the sidewall 16 of the container 12.

Figure 9:
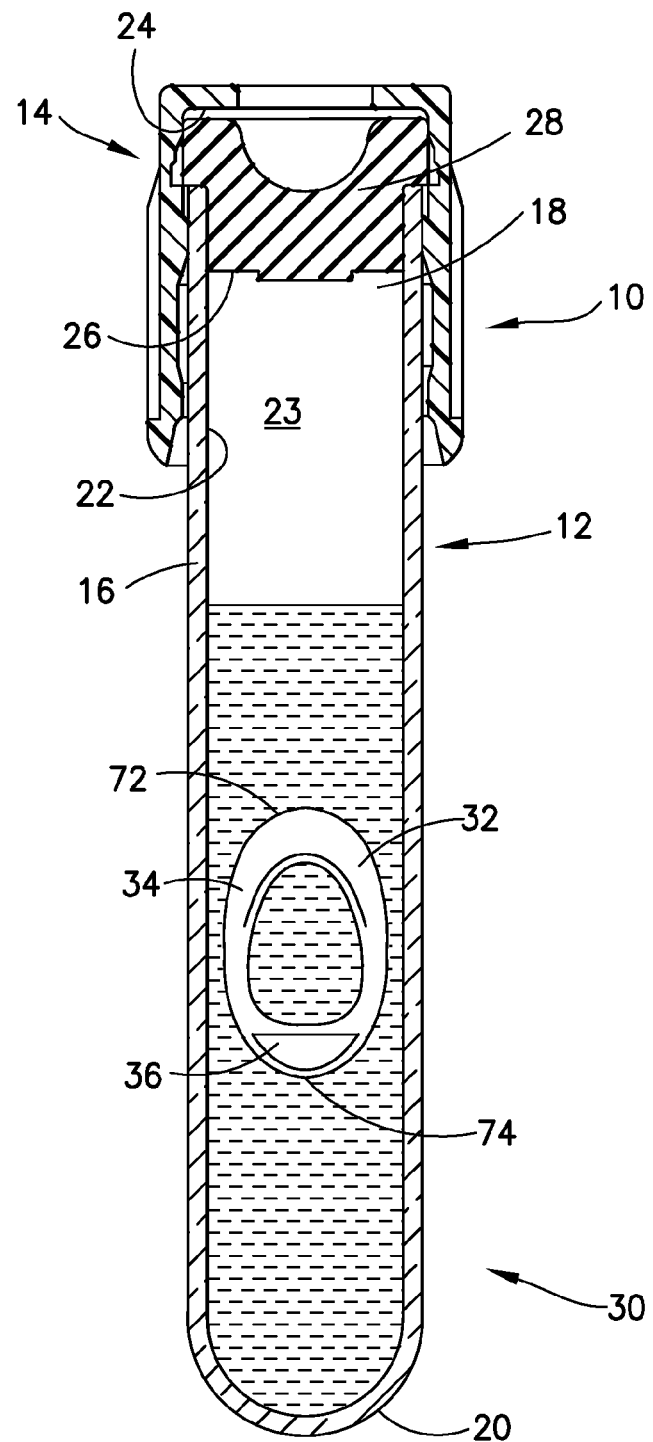
FIG. 9 is a partial cross-sectional front view of a separation assembly wherein the mechanical separator disposed within the container is in an intermediate position for allowing fluid to pass around the mechanical separator in accordance with an embodiment of the present invention.

Upon application of rotational force, such as during centrifuge, and transition of the mechanical separator 30 as shown in FIG. 9, the mechanical separator 30 experiences a rotational moment, deforms sufficiently to disengage from the first position engagement with the container 12, and rotates in a clockwise direction. In the embodiment, shown in FIGS. 8-10, where the first part 34 is a float and the second part 36 is a ballast, the mechanical separator 30 will be oriented with the second part 36 facing the bottom closed second end 20 of the container 12.

Once the mechanical separator 30 contacts the fluid contained within the container 12, air that occupies the through-hole 38 is progressively displaced by the fluid as the device submerges. When the mechanical separator 30 is submerged in the fluid, the difference in the buoyancy between the first part 34 and the second part 36 generates a differential force across the mechanical separator 30. During centrifugation, the differential force causes the separator body 32 to elongate and contract away from the sidewall 16 of the collection container 12, thereby reducing the effective diameter of the separator body 32 and opening a communicative pathway for the flow of fluid, such as higher and lower density phase components, past the separator body 32. It is noted that the first part 34 may be adapted for deformation in directions substantially perpendicular to the through-hole 38.

Because, in the first position, the through-axis T of the through-hole 38 is offset from the longitudinal axis L of the container 12, upon introduction of the fluid into the container 12, there is little or no pooling of fluid in an area 86 adjacent to the contact point between the second portion 36 of the mechanical separator 30 and the sidewall 16 of the container 12. This is also the case for the pooling of fluid that would occur in an area 86a adjacent to the contact point between the first portion 34 of the mechanical separator 30 and a sidewall 16 of the container 12. Further, during rotation, the mechanical separator 30 only minimally contacts or does not contact at all any pooled fluid in this area 86. Therefore, the pooled fluid is not subjected to any forces from the mechanical separator 30 that could cause cellular damage to the fluid.

Likewise, in the first position, while some fluid may pool in an area 88 adjacent to the contact point between the first portion 34 of the mechanical separator 30 and the sidewall 16 of the container 12, during rotation, very little of the mechanical separator 30 will contact the pooled fluid in this area 88, and the pooled fluid is not subjected to any forces from the mechanical separator 30 that could cause cellular damage to the fluid.

Figure 10:
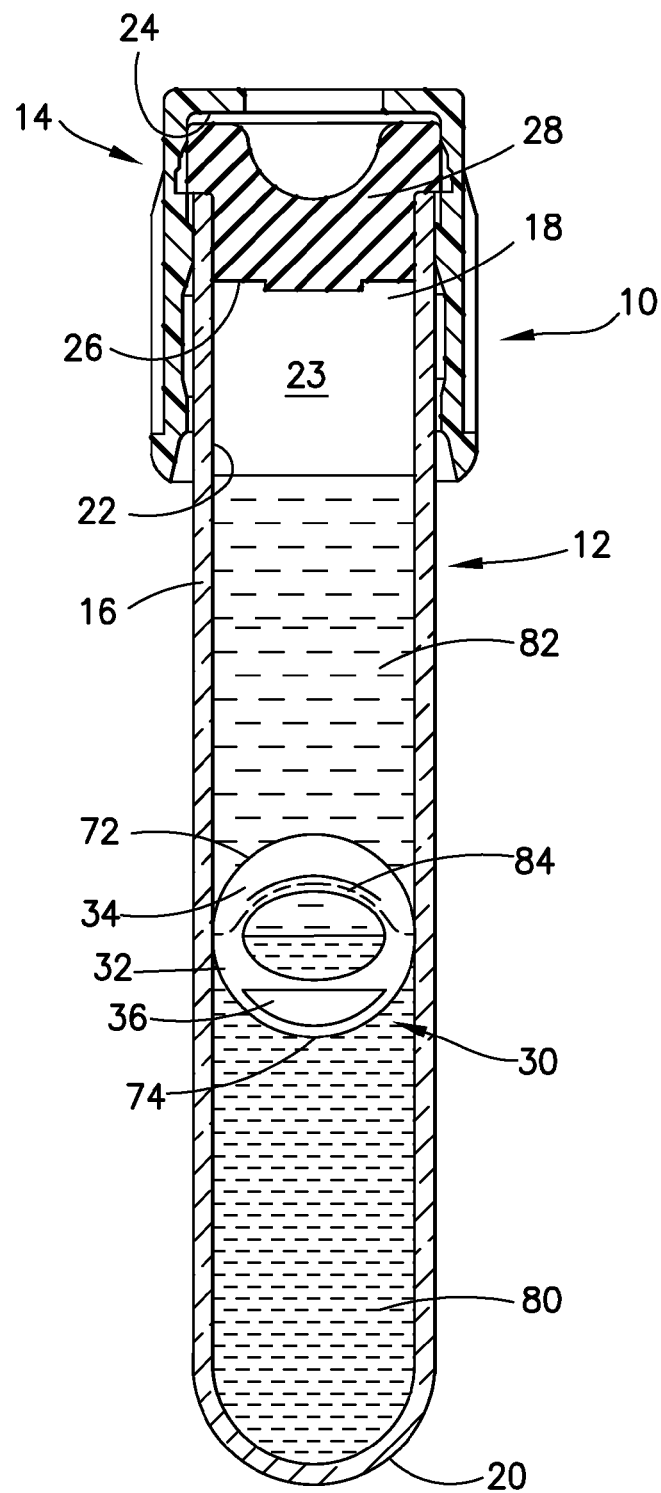
FIG. 10 is a partial cross-sectional front view of a separation assembly wherein the mechanical separator is disposed within the container in a second position in accordance with an embodiment of the present invention.

Once the application of rotational force has ceased, the mechanical separator 30 becomes oriented between a separated higher density phase 80 and a separated lower density phase 82 in a second sealing position (FIG. 10). At the same time, the elongation of the separator body 32 ceases, causing the separator body 32 to return to its initial configuration, thereby forming a seal where the separator body 32 contacts the sidewall 16 of the container 12 at at least part of a periphery 84 of the upper surface 72 of the separator body 32. The separator body 32 may contact the sidewall 16 of the container 12 at the entire periphery 84 of the upper surface 72 of the separator body 32. In the embodiment where the first part 34 is a float, the periphery 84 of the upper surface 72 is part of the float. In this position, the through-hole 38 is substantially perpendicular to longitudinal axis L of the container 12.

The periphery 84 of the upper surface 72 of the separator body 32 has an outer circumference that is at least slightly larger than the corresponding interior circumference of the sidewall 16 of the container 12. In addition, the smallest diameter $D_1$ of the top surface of the first part 34 is at least slightly greater than the corresponding diameter of the inner surface 22 of the container 12. Accordingly, the mechanical separator 30 is adapted to prevent fluid from passing between or around the separator body 32 and the container 12, and also prevents fluid from passing through the through-hole 38, effectively establishing a barrier and the periphery 84 of the upper surface 72 of the separator body 32 establishes a barrier between higher and lower density phases 80, 82 within the sample.

As can be determined from the discussion above, the separator body 32 is in a compressed, but substantially unstressed state when it forms a seal with the interior surface 22 of the sidewall 16 of the container 12. The shape of the top profile of the separator body 32 provides for this compression to form a tight seal with the interior surface 22 of the sidewall 16 of the container 12. The interior surface 22 of the sidewall 16 of the container 12 has a first shape that is substantially circular, while the separator body 32 has a top surface that defines a second periphery shape 84 that is non-circular in the uncompressed state.

While the present invention is described with reference to several distinct embodiments of a mechanical separator assembly and method of use, those skilled in the art may make modifications and alterations without departing from the scope and spirit. Accordingly, the above detailed description is intended to be illustrative rather than restrictive.

The invention claimed is:

1. A separation assembly for enabling separation of a fluid into first and second parts, comprising:
   a container having a first end, a second end, and a sidewall extending therebetween having an inner surface and defining a container interior, the container defining a longitudinal axis between the first end and the second end; and
   a separator body disposed within the container interior and having a through-hole comprising a straight bore defined therethrough, the separator body comprising:
   a first part; and
   a second part interfaced with the first part,
   wherein the separator body is transitionable from a first position in which the through-hole is provided in fluid-receiving alignment with the first end of the container, to a second position in which the through-hole is provided substantially perpendicular to the longitudinal axis of the container, and
   wherein, in the first position, a first perimeter of the separator body forms an interference engagement with the sidewall of the container and a through-axis of the through-hole of the separator body is in a plane that is not parallel with a plane containing the longitudinal axis of the container.

2. The separation assembly of claim 1, wherein the first part of the separator body is a float and the float defines an upper surface of the separator body, and the second part of the separator body is a ballast and the ballast defines a lower surface of the separator body.

3. The separation assembly of claim 2, wherein the first perimeter is offset from a center of the upper surface of the float.

4. The separation assembly of claim 2, wherein the first perimeter is offset from a center of the lower surface of the ballast.

5. The separation assembly of claim 2, wherein the separator body comprises a second perimeter defined by at least part of a periphery of the upper surface of the float and, in the second position, the second sealing perimeter of the separator body contacts the sidewall of the container.

6. The separation assembly of claim 2, wherein the separator body comprises a second perimeter defined by the entire periphery of the upper surface of the float and, in the second position, the second sealing perimeter of the separator body contacts the sidewall of the container.

7. The separation assembly of claim 1, wherein a part of the first part of the separator body and a part of the second part of the separator body define the through-hole.

8. The separation assembly of claim 1, wherein the first part of the separator body defines the through-hole.

9. A separation assembly for enabling separation of a fluid into first and second parts, comprising:
   a container having a first end, a second end, and a sidewall extending therebetween having an inner surface and defining a container interior, the container defining a longitudinal axis between the first end and the second end; and
   a separator body disposed within the container interior and having a through-hole comprising a straight bore defined therethrough, the separator body comprising:
   a first part; and
   a second part interfaced with the first part,
   wherein the separator body is transitionable from a first position in which the through-hole is provided in fluid-receiving alignment with the first end of the container, to a second position in which the through-hole is provided substantially perpendicular to the longitudinal axis of the container, and
   wherein, in the first position, a first perimeter of the separator body forms an interference engagement with the sidewall of the container and a through-axis of the through-hole is angled with respect to at least one of the longitudinal axis of the container and the sidewall of the container.

10. The separation assembly of claim 9, wherein, in the first position, the through-axis of the through-hole is angled from about 30° to about 60° with respect to the sidewall of the container.

11. The separation assembly of claim 9, wherein the first part of the separator body is a float and the float defines an upper surface of the separator body, and the second part of the separator body is a ballast and the ballast defines a lower surface of the separator body.

12. The separation assembly of claim 11, wherein the first perimeter is offset from a center of the upper surface of the float.

13. The separation assembly of claim 11, wherein the first perimeter is offset from a center of the lower surface of the ballast.

14. The separation assembly of claim 11, wherein the separator body comprises a second perimeter defined by at least part of a periphery of the upper surface of the float and, in the second position, the second sealing perimeter of the separator body contacts the sidewall of the container.

15. The separation assembly of claim 11, wherein the separator body comprises a second perimeter defined by the entire periphery of the upper surface of the float and, in the second position, the second sealing perimeter of the separator body contacts the sidewall of the container.

16. The separation assembly of claim 9, wherein a part of the first part of the separator body and a part of the second part of the separator body define the through-hole.

17. The separation assembly of claim 9, wherein the first part of the separator body defines the through-hole.

18. A separation assembly for enabling separation of a fluid into first and second parts, comprising:
   a container having a first end, a second end, and a sidewall extending therebetween having an inner surface and defining a container interior, the container defining a longitudinal axis between the first end and the second end; and
   a separator body disposed within the container interior and having a through-hole comprising a straight bore defined therethrough, the separator body comprising:
   a first part; and
   a second part interfaced with the first part,
   wherein the separator body is transitionable from a first position in which the through-hole is provided in fluid-receiving alignment with the first end of the container, to a second position in which the through-hole is provided substantially perpendicular to the longitudinal axis of the container, and wherein, in the first position, a first perimeter of the separator body forms an interference engagement with the sidewall of the container and a through-axis of the through-hole of the separator body is offset from the longitudinal axis of the container.

19. The separation assembly of claim 18, wherein the first part of the separator body is a float and the float defines an upper surface of the separator body, and the second part of the separator body is a ballast and the ballast defines a lower surface of the separator body.

20. The separation assembly of claim 19, wherein the first perimeter is offset from a center of the upper surface of the float.

21. The separation assembly of claim 19, wherein the first perimeter is offset from a center of the lower surface of the ballast.

22. The separation assembly of claim 19, wherein the separator body comprises a second perimeter defined by at least part of a periphery of the upper surface of the float and, in the second position, the second sealing perimeter of the separator body contacts the sidewall of the container.

23. The separation assembly of claim 19, wherein the separator body comprises a second perimeter defined by the entire periphery of the upper surface of the float and, in the second position, the second sealing perimeter of the separator body contacts the sidewall of the container.

24. The separation assembly of claim 18, wherein a part of the first part of the separator body and a part of the second part of the separator body define the through-hole.

25. The separation assembly of claim 18, wherein the first part of the separator body defines the through-hole.

26. A separation assembly for enabling separation of a fluid into first and second parts, comprising:

a container having a first end, a second end, and a sidewall extending therebetween having an inner surface and defining a container interior, the container defining a longitudinal axis between the first end and the second end; and a separator body disposed within the container interior and having a through-hole comprising a straight bore defined therethrough, the separator body comprising:

a float; and a ballast, wherein the float and the ballast are connected, the ballast defining a leading ballast part and a trailing ballast part, wherein the separator body is transitionable from a first position in which the separator body is in contact with the sidewall of the container and the through-hole is provided in fluid-receiving alignment with the first end of the container, to a second position in which the through-hole is provided substantially perpendicular to the longitudinal axis of the container, and wherein, in the first position, a first perimeter of the separator body forms an interference engagement with the sidewall of the container, wherein the first perimeter extends around the leading ballast part of the separator body and is offset from the trailing ballast part.

27. The separation assembly of claim 26, wherein the float defines a leading float part and a trailing float part, and wherein the first perimeter extends around the trailing float part and the leading ballast part of the separator body and is offset from the leading float part and the trailing ballast part.

* * * * *